United States Patent [19]

Elmqvist

[11] 4,321,928
[45] Mar. 30, 1982

[54] HEART PACEMAKER

[75] Inventor: Hakan Elmqvist, Bromma, Sweden

[73] Assignee: Siemens Aktiengesellschaft, Berlin & Munich, Fed. Rep. of Germany

[21] Appl. No.: 188,518

[22] Filed: Sep. 18, 1980

[30] Foreign Application Priority Data

Sep. 27, 1979 [DE] Fed. Rep. of Germany ....... 2939233

[51] Int. Cl.³ ............................................. A61N 1/36
[52] U.S. Cl. ............................................. 128/419 PG
[58] Field of Search ...................... 128/419 PG, 419 D

[56] References Cited

U.S. PATENT DOCUMENTS

| | | | |
|---|---|---|---|
| 3,431,912 | 3/1969 | Keller, Jr. | 128/419 PG |
| 3,726,285 | 4/1973 | Bowers et al. | 128/419 PG |
| 4,050,004 | 9/1977 | Greatbatch | 128/419 PG |
| 4,132,233 | 1/1979 | Hartlaub | 128/419 PG |
| 4,203,448 | 5/1980 | Keller, Jr. | 128/419 PG |
| 4,248,238 | 2/1981 | Joseph | 128/419 PG |

FOREIGN PATENT DOCUMENTS

| | | | |
|---|---|---|---|
| 85383 | 6/1965 | France | 128/419 D |
| 826766 | 1/1960 | United Kingdom | 128/419 PG |

Primary Examiner—William E. Kamm
Attorney, Agent, or Firm—Hill, Van Santen, Steadman, Chiara & Simpson

[57] ABSTRACT

In the exemplary embodiments, the processing circuit for supplying the stimulation pulses comprises a series arrangement of capacitors which are chargeable in parallel and dischargeable serially. The goal of the disclosure, given such a heart pacemaker, is to see to the greatest possible variability of the output amplitude given the lowest possible technical outlay. This goal is inventively achieved in that program switches are allocated to the capacitor circuit for interconnecting or, respectively, disconnecting individual capacitors in combination randomly prescribable as needed for parallel charging and/or serial discharge, said interconnection or, respectively, disconnection occurring according to programs of a program generator.

7 Claims, 7 Drawing Figures

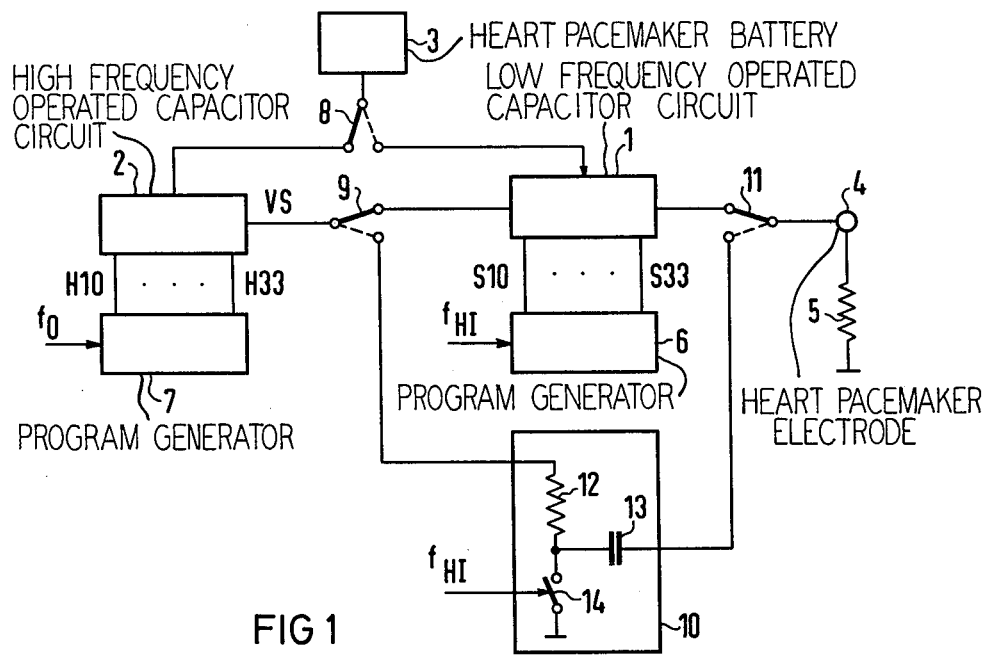
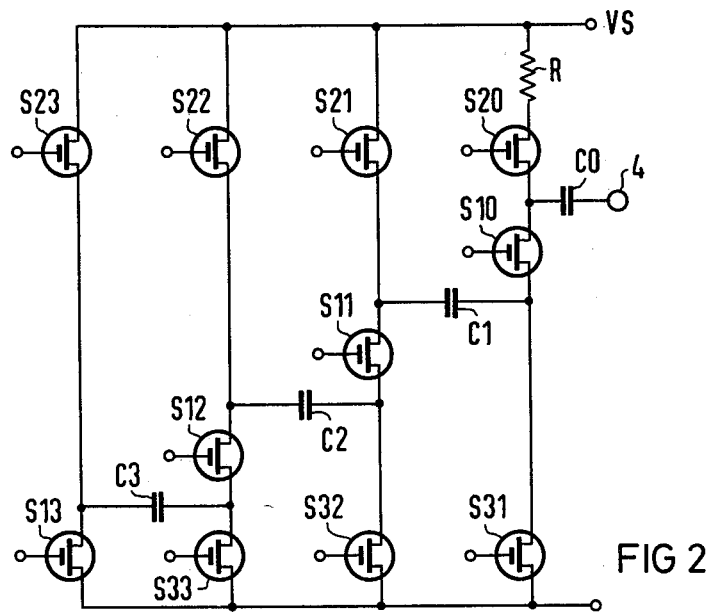

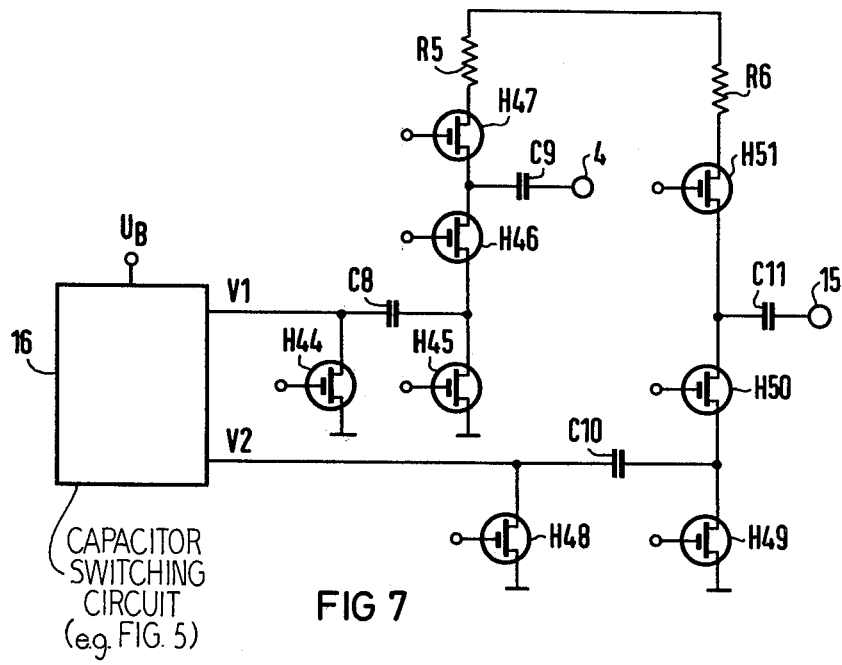

HEART PACEMAKER

BACKGROUND OF THE INVENTION

The invention relates to a heart pacemaker with a clock pulse generator and shaping circuit for supplying the stimulation pulses in addition to an operating voltage generator, particularly a battery, wherein the shaping circuit comprises a series arrangement of capacitors which are chargeable in parallel and dischargeable serially.

A heart pacemaker of this type is known, for example, from the U.S. Pat. No. 4,050,004. This heart pacemaker functions with a battery voltage of approximately 2.5 V. Given a total of four capacitors, there derives an output voltage of approximately 10 V given parallel charging and serial discharging. Such an output voltage, however, is not always optimally adapted to the actual ambient conditions of the pacemaker. It is often the case that a pacemaker is desired whose output amplitude is variable according to prescribable need. For example, a step-shaped course of the stimulation amplitude can be desirable for the purpose of measuring the stimulus threshold of the pacemaker-assisted heart. Under certain conditions, other courses of the amplitude of the stimulation pulses can be desirable for other purposes. Overall, however, the heart pacemaker should always be laid out in terms of energy in such manner that the battery is loaded as little as possible after implantation, so that a longer useful life derives for the implanted pacemaker. For this reason, too, the pacemaker should be as variable as possible in the output amplitude of its pacemaker pulses.

SUMMARY OF THE INVENTION

The object of the invention is to construct a pacemaker of the type initially cited which offers greater variation possibilities with respect to the output amplitude than hitherto.

This object is inventively achieved in that program switches are allocated to the capacitor circuit, said program switches interconnecting or, respectively, disconnecting individual capacitors in combinations randomly prescribable as needed for parallel charging and/or serial discharging, said interconnection or, respectively, disconnection occurring according to programs of a program generator.

The heart pacemaker according to the invention enables the preselection of the amplitude course of the heart pacemaker pulses according to program. Accordingly, it can always be quickly and optimally adapted from outside to the requirements of the moment.

As viewed overall, there is also a desire in heart pacemakers for a particularly compact structure, since, thereby, the pacemaker becomes smaller overall as to its dimensions. In an advantageous development of the invention, there thereby derive optimum conditions when the capacitors and program switches are components of a combination consisting of a shaping circuit operated low-frequency-wise and a shaping circuit operated high-frequency-wise. In such a case, there is the possibility of variation in a wide voltage range (for example between 2.5 V and 40 V), given capapcitor volumes which are optimally matched to one another. As is known, capacitors in shaping circuits operated low-frequency-wise exhibit relatively high capacitance. In order to realize these large capacitances, appropriately large-volume capacitors must be employed. A shaping circuit operated high-frequency-wise, on the other hand, can function with smaller capacitances and, thus, with less voluminous capacitors. A healthy mixture of both operating modes, thus, guarantees an optimally broad voltage variation range given an optimally low space outlay for capacitors. A shaping circuit operated high-frequency-wise, further, also has the advantage of a smaller time constant of the RC elements. It is accordingly particularly well suited for detecting heart activity potentials via the heart pacemaker electrode. The detected signals can be employed as recognition signals for spontaneous heart reactions in order to inhibit the pacemaker. In order to be able to employ a heart pacemaker according to the present invention as versatilely as possible, a far-reaching, variable changeover possibility, a far-reaching, variable changeover possibility between low-frequency-wise and high-frequency-wise operation or, respectively, the combination of both should be guaranteed. Thus, switches should be provided which guarantee an operating mode solely in the low-frequency range or in the high-frequency range or in the combination of both. The circuit arrangement should also be such that, in a simple modification, a second output which renders connection to a second heart pacemaker electrode possible is respectively created for one or both operating modes. A bifocal pacemaker is thereby created which renders possible stimulation of both heart chambers, for example, in the atrium and in the ventricle, as needed.

Further advantages and details of the invention derive from the following description of an exemplary embodiment on the basis of the accompanying drawing sheets in conjunction with the subclaims; and other objects, features and advantages will be apparent from this detailed disclosure and from the appended claims.

BRIEF DESCRIPTION OF THE DRAWINGS

FIG. 1 is a circuit diagram for illustrating an embodiment of the invention;

FIG. 2 shows a shaping or capacitor circuit operated low-frequency-wise for use in FIG. 1;

FIGS. 5 through 7 show two modification possibilities for the shaping circuit operable high-frequency-wise for conversion to bifocal operation.

DETAILED DESCRIPTION

Figure 3:
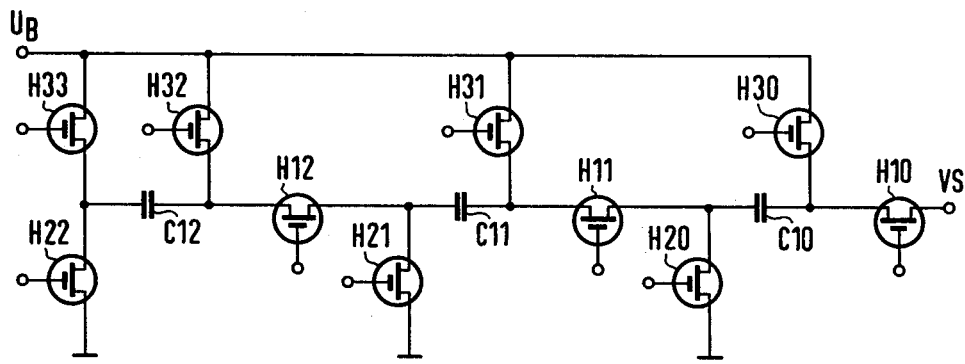
FIG. 3 shows a shaping or capacitor circuit operated high-frequency-wise for use in FIG. 1.
Figure 4:
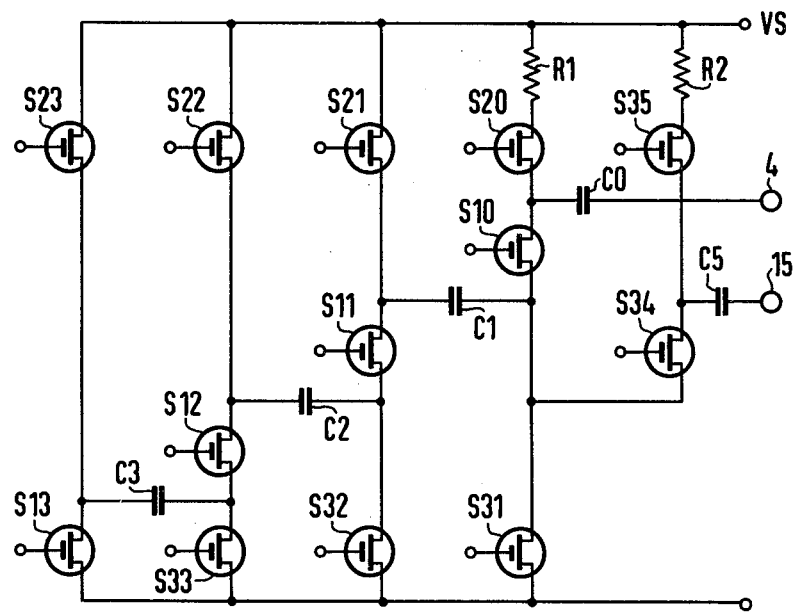
FIG. 4 shows a modification possibility of the shaping circuit operable low-frequency-wise for conversion to bifocal operation.
Figure 5:
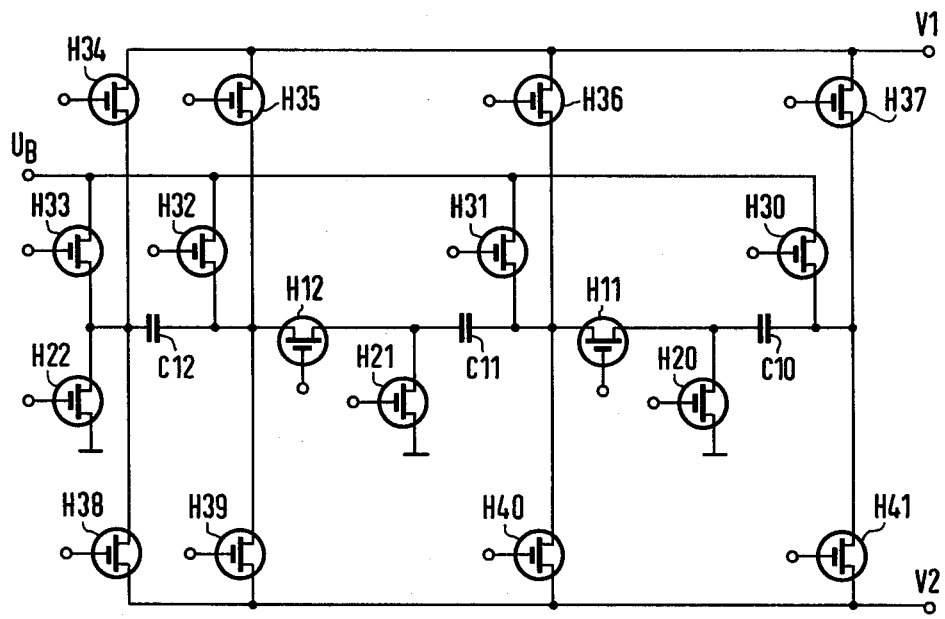

In FIG. 1, a shaping [or: printed?] circuit to be operated low-frequency-wise is referenced with 1. The reference numeral 2 indicates a shaping or capacitor circuit to be operated high-frequency-wise. The battery of the heart pacemaker is referenced with 3. The heart pacemaker electrode is referenced with 4. It lies against the human heart 5 schematically illustrated as a resistance. A program generator 6 with program outputs S10 through S33 is allocated to the shaping circuit 1 to be operated low high frequency-wise. Accordingly, the shaping or capacitor circuit 2 to be operated high-frequency-wise comprises a program generator 7 with program outputs H10 through H33. The program generator 7 is serviced high-frequency-wise with the clock frequency $f_o$ which has a frequency in the range from about 100 Hz through about 10 kHz. The control of the program generator 6 ensues low-frequency-wise with the clock frequency of the pacemaker pulses $f_{HI}$ ($f_{HI}$ may represent a frequency of about one hertz, 1 Hz). The circuit diagram of FIG. 1 allows optimum variation of the operating possibilities by means of switches 8, 9, 10 and 11. In the illustrated swtich position of the individual switches, the two shaping circuits for low-frequency-wise and high-frequency-wise operation are connected in series. At the output, thus, there derive voltage variation possibilities between, for example, 0 through 40 V. By switching the switches 9 and 11 into the switch position illustrated with broken lines, exclusively high-frequency-wise operation ensues via the switching element 10 comprising the RC element 12, 13 and the switch 14, clocked in the clock pulse of the heart frequency $f_{HI}$. When the switch 8 is switched into the switch position indicated with broken lines, exclusively low-frequency-wise operation ensues. By means of activating only one of the two operating modes, the voltage can be accordingly varied in lower ranges.

FIG. 2 shows an embodiment of the shaping or capacitance circuit 1 to be operated low-frequency-wise. It comprises four capacitors C0 through C3 with appertaining transistor switches S10 through S33. All switches S10 through S33 can be driven into the conductive state individually or in combination as desired according to the program of the program generator 6.

An example of a shaping or capacitor circuit 2 to be operated high-frequency-wise is shown in FIG. 3. This shaping circuit exhibits the three capacitors C10 through C12. The switches H10 through H33 are again actuatable by the program generator individually or in combination as desired.

FIGS. 4 through 7 show modifications of these two embodiments with new output stages S34, S35, R2, C5 (FIG. 4) or, respectively H34 through H41 (FIG. 5) in combination with H42, H43, R3, R4, C6, C7 (FIG. 6) or H44 through H51, C8 through C11, R5, R6 (FIG. 7) to that end that a second output is created for a second electrode terminal 15. By so doing, there derives a bifocal pacemaker with the possibility of employing two stimulation electrodes, for example, for the stimulation of the atrium and/or of the ventricle. Thereby, the block 16 in FIGS. 6 and 7 corresponds to the circuit diagram of FIG. 5.

It will be apparent that many modifications and variations may be effected without departing from the scope of the novel concepts and teachings of the present invention.

I claim as my invention:

1. A heart pacemaker with clock pulse generator and a processing circuit for supplying the stimulation pulses, and an operating voltage generator, in particular a battery, the processing circuit comprising capacitor circuit means including capacitors which can be charged in parallel and discharged serially, characterized in that the capacitor circuit means (C0 through C3; C10 through C12) has a program generator (6; 7), and program switches (S10 through S33; H10 through H33) assigned to it which interconnect or, respectively, disconnect individual capacitors in combinations randomly prescribable as needed for parallel charging and/or serial discharge, said interconnection or, respectively, disconnection occurring under the control of said program generator (6; 7).

2. A heart pacemaker according to claim 1, characterized in that the capacitors and program switches are a component of a capacitor circuit (1) operated low-frequency-wise or of a capacitor circuit (2) operated high-frequency-wise or are a component of a combination consisting of capacitor circuits (1 and 2) operated low-frequency-wise and high-frequency-wise.

3. A heart pacemaker according to claim 2, characterized in that, upon employment of a capacitor circuit operated low-requency-wise and/or high-frequency-wise, said processing circuit comprising capacitors and program switches, a corresponding program generator (6, 7) is allocated to each capacitor circuit (1, 2).

4. A heart pacemaker according to claim 1, characterized in that program switches in the form of switching transistors are present both in the charge as well as in the discharge paths of the capacitors.

5. A heart pacemaker according to claim 1, characterized in that tapping locations for the connection of a second heart pacemaker electrode (15) are allocated to the capacitor paths.

6. A heart pacemaker according to claim 5, characterized in that, a capacitor circuit to be operated low-frequency-wise is employed, and an auxiliary output for a second heart pacemaker electrode (15) is created by means of an output parallel circuit consisting of switching elements (S34, S35, R2, C5, FIG. 4).

Figure 6:
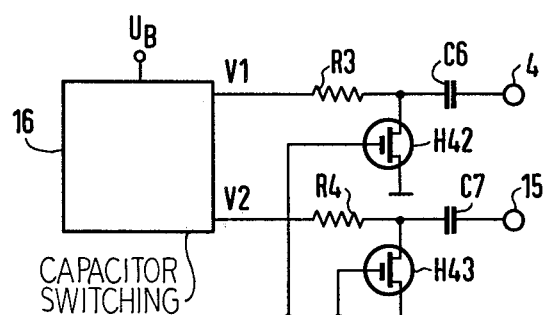

7. A heart pacemaker according to claim 5, characterized in that, a capacitor circuit to be operated high-frequency-wise is employed, and a double series of switches (H34 through H37, H38 through H41, FIG. 5) is present for each capacitor (C10 through C12 instead of the single output stage (H10, VS) in order to create two separate voltage courses (V1, V2), to which two further output stages (H42, H43, R3 R4, C6, C7; FIG. 6; H44 through H51, C8 through C11, R5, R6, FIG. 7) for two separate heart pacemaker electrodes (4, 15) are allocated.

* * * * *